(12) United States Patent
Geliot et al.

(10) Patent No.: US 12,364,632 B2
(45) Date of Patent: Jul. 22, 2025

(54) ASSEMBLY HAVING A STRUCTURE AND A RESERVOIR FASTENED TO THE STRUCTURE AND CONTAINING AN EXTINGUISHING FLUID

(71) Applicant: Airbus Operations (S.A.S.), Toulouse (FR)

(72) Inventors: Jean Geliot, Toulouse (FR); Adeline Soulie, Toulouse (FR); Frédéric Goupil, Toulouse (FR); Solène Cruaud Prieur, Toulouse (FR)

(73) Assignee: Airbus Operations (S.A.S.), Toulouse (FR)

( * ) Notice: Subject to any disclaimer, the term of this patent is extended or adjusted under 35 U.S.C. 154(b) by 562 days.

(21) Appl. No.: 17/854,865

(22) Filed: Jun. 30, 2022

(65) Prior Publication Data

US 2023/0000697 A1    Jan. 5, 2023

(30) Foreign Application Priority Data

Jul. 2, 2021 (FR) ...................................... 2107205

(51) Int. Cl.
*A61F 13/58* (2006.01)
*A62C 13/78* (2006.01)
(Continued)

(52) U.S. Cl.
CPC ............ *A61F 13/581* (2013.01); *A62C 13/78* (2013.01); *F16B 41/002* (2013.01); *F16B 39/24* (2013.01); *F16M 11/04* (2013.01)

(58) Field of Classification Search
CPC ....... A61F 13/581; A62C 13/78; A62C 13/00; A62C 13/76; A62C 35/02; A62C 35/023; A62C 35/13; A62C 31/28
See application file for complete search history.

(56) References Cited

U.S. PATENT DOCUMENTS

| 2010/0230122 A1* | 9/2010 | Machado ................. A62C 3/08 |
| | | 169/62 |
| 2019/0151690 A1 | 5/2019 | Kho et al. |
| 2021/0101694 A1* | 4/2021 | Cayssials ............... B64D 37/32 |

FOREIGN PATENT DOCUMENTS

| CN | 210 845 048 U | 6/2020 |
| CN | 211 584 982 U | 9/2020 |

(Continued)

OTHER PUBLICATIONS

French Search Report for Application No. 2107205 dated Feb. 23, 2022.

*Primary Examiner* — Christopher R Dandridge
(74) *Attorney, Agent, or Firm* — KDW Firm PLLC

(57) ABSTRACT

An assembly having a chassis, two supports with a plate and a guide, a nesting system with a bore, a reservoir containing an extinguishing fluid and with two fastening tabs, two bearing tabs and a peg, and a fastener. The reservoir is able to move in translation between a premounting position in which each fastening and bearing tab rests on a plate and each guide guides the fastening and bearing tabs to align the peg and the bore, and a mounting position in which each fastening tab rests on the plate, the peg is introduced into the bore, the bearing tabs no longer rest on the plates and the fastener fastens each fastening tab to the plate. Such an assembly allows the reservoir to be withdrawn and put in place quickly and easily.

7 Claims, 5 Drawing Sheets

(51) Int. Cl.
*F16B 41/00* (2006.01)
*F16B 39/24* (2006.01)
*F16M 11/04* (2006.01)

(56) References Cited

FOREIGN PATENT DOCUMENTS

EP 3 305 372 A1 4/2018
FR 3 105 177 A1 6/2021

* cited by examiner

ASSEMBLY HAVING A STRUCTURE AND A RESERVOIR FASTENED TO THE STRUCTURE AND CONTAINING AN EXTINGUISHING FLUID

CROSS-REFERENCE TO RELATED APPLICATION

This application claims priority to French patent application number 2107205 filed on Jul. 2, 2021, the entire disclosure of which is incorporated by reference herein.

TECHNICAL FIELD

The disclosure herein relates to an assembly having a structure and a reservoir containing an extinguishing fluid and fastened to the structure, and also to an aircraft having at least one such assembly.

BACKGROUND

An aircraft conventionally has at least one nacelle inside which an engine, for example of the jet engine type, is disposed. The nacelle and the engine are fastened to the structure of the aircraft by a pylon fastened beneath the wing of the aircraft.

In order to avoid the structure of the aircraft becoming damaged in the event of the engine catching fire, the aircraft is equipped with a fire-fighting system that conventionally has two reservoirs.

Currently, the extinguishing fluid contained in the reservoirs is a product called "halon". For environmental protection reasons, new products will gradually replace halon, but in order to obtain the same result in terms of extinguishing power, it is necessary to use a greater volume of these new products, and this also leads to reservoirs with larger dimensions and a greater mass.

Reservoirs are conventionally mounted in a pylon that holds the nacelle and the inside of such a pylon is a relatively cluttered location. The enlargement of the reservoirs does not make it easier to mount them inside the pylon, and it is therefore necessary to find an arrangement that allows easier mounting of each reservoir.

SUMMARY

An object of the disclosure herein is an assembly for an aircraft, wherein the assembly has a structure that is fastened to a structure of the aircraft and a reservoir containing an extinguishing fluid, and wherein the installation of the reservoir on the structure is made easier.

To this end, an assembly comprises:
a structure having a chassis, two supports and a nesting system fastened to the chassis and having a bore with an opening and of which the axis is parallel to a direction of introduction, wherein each support has a plate fastened to the chassis and a guide as one with the plate,
a reservoir containing an extinguishing fluid, and having two fastening tabs, two bearing tabs distinct from the fastening tabs, and a peg of which the axis is parallel to the direction of introduction, and
a fastener,
wherein the reservoir is arranged so as to be able to move in translation parallel to the direction of introduction between a premounting position in which each fastening tab and each bearing tab rest on one of the plates and each guide guides the fastening tab and the bearing tab that are associated with the plate transversely with respect to the direction of introduction so as to align the peg and the opening of the bore of the nesting system, and a mounting position in which each fastening tab rests on the associated plate, the peg is introduced into the opening of the bore of the nesting system, the bearing tabs no longer rest on the plates, and the fastener fastens each fastening tab to the associated plate.

Such an assembly allows the reservoir to be withdrawn and put in place quickly and easily.

Advantageously, each plate is fastened to the chassis by at least one damping system.

Advantageously, each damping system has:
a screw with a head and a threaded shank,
a nut,
a first ring made of elastomer that has a first shoulder,
a second ring made of elastomer that has a second shoulder,
an outer bearing as one with the plate,
wherein the first ring is threaded onto the threaded shank with the first shoulder against the head, the outer bearing is threaded onto the threaded shank and is fitted onto the first ring, the second ring is threaded onto the threaded shank, being fitted beneath the outer bearing and with the second shoulder away from the first shoulder and bearing against the chassis, the threaded shank is introduced into a bore of the chassis and the nut is tightened on the threaded shank on the other side of the chassis with respect to the head.

Advantageously, the damping system has an inner bearing threaded onto the threaded shank and on which the two rings are fitted.

Advantageously, the damping system has a washer beneath the head of the screw.

Advantageously, the nesting system has:
an inner tube of which the bore forms the bore for housing the peg,
an outer tube coaxial with the inner tube, disposed outside the inner tube, and fastened to the chassis, and
an intermediate tube made of elastomer that is fastened between the inner tube and the outer tube.

The disclosure herein also proposes an aircraft having a pylon of which one wall has a window, an assembly according to one of the preceding variants, wherein the chassis is fastened inside the pylon and wherein the opening of the bore is oriented towards the window.

BRIEF DESCRIPTION OF THE DRAWINGS

The abovementioned features of the disclosure herein, along with others, will become more clearly apparent upon reading the following description of one example embodiment, the description being given with reference to the appended drawings, in which.

DETAILED DESCRIPTION

Figure 1:
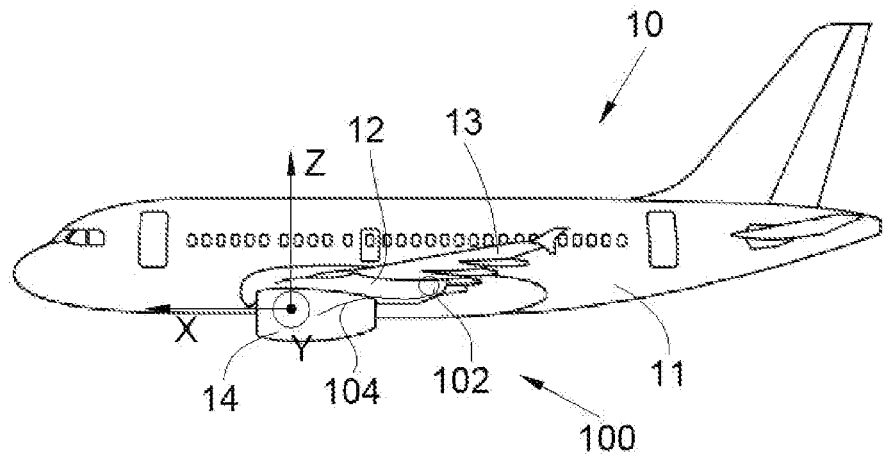
FIG. 1 is a side view of an aircraft according to the disclosure herein.

In the following description, terms relating to a position are considered in relation to an aircraft in a normal flight position, i.e. as shown in FIG. 1.

In the following description, and by convention, the X direction is the longitudinal direction of the jet engine, which is parallel to the longitudinal axis of the aircraft, the Y direction is the transverse direction, which is horizontal when the aircraft is on the ground, and the Z direction is the vertical direction, which is vertical when the aircraft is on the ground, these three directions X, Y and Z being mutually orthogonal.

FIG. 1 shows an aircraft 10 that has a fuselage 11 to each side of which is fastened a wing 13 that bears an engine 14 such as a turbofan, for example.

For each engine 14, the aircraft 10 also has a pylon 12 that fastens the engine 14 beneath the wing 13.

For each engine 14, the aircraft 10 has a fire-fighting system 100 that has at least one reservoir 102 and, for each reservoir 102, a discharge pipe 104 that extends between the reservoir 102 and the engine 14 supported by the pylon 12.

Figure 2:
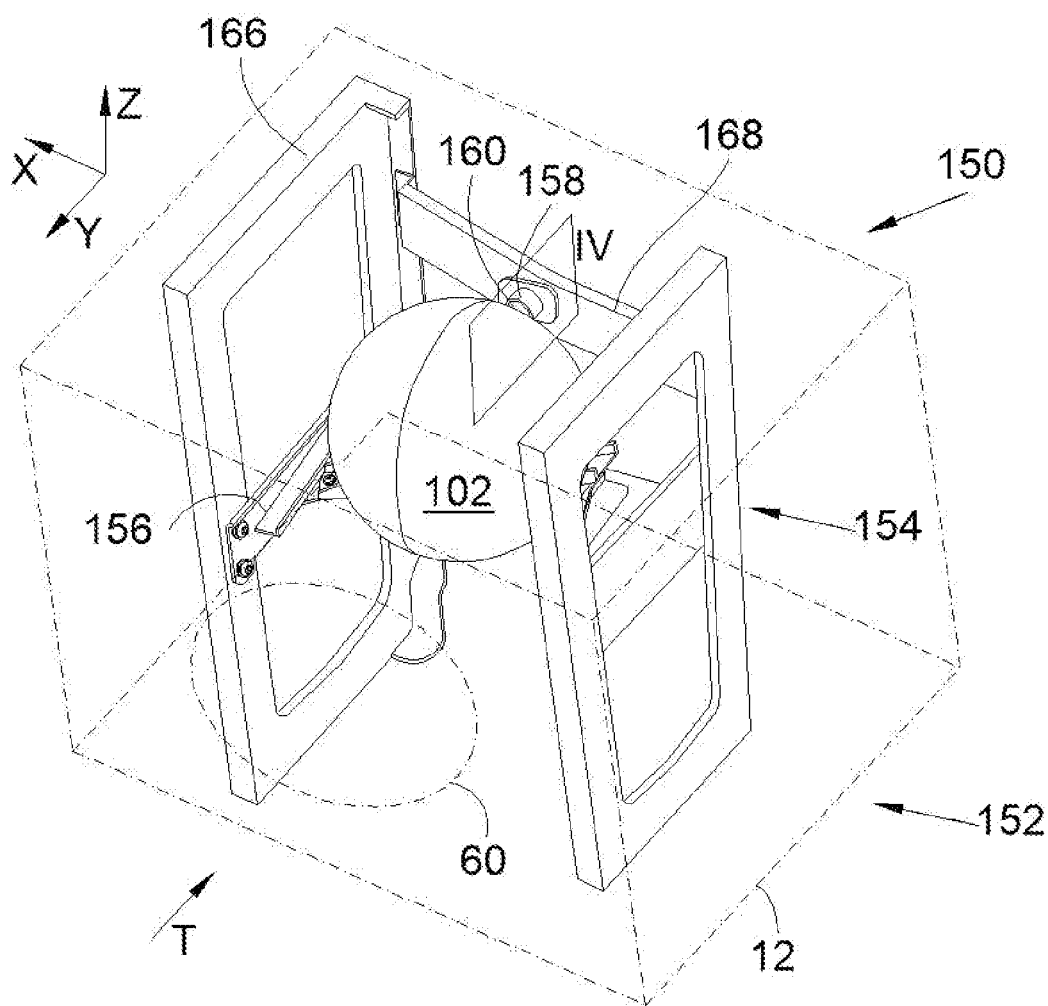
FIG. 2 is a perspective view of an assembly according to the disclosure herein with the reservoir.

FIG. 2 shows an assembly 150 according to the disclosure herein that has a structure 152 and a reservoir 102 fastened to the structure 152. The assembly 150 is housed inside the pylon 12 that is depicted here by way of dot-dashed lines. Conventionally the reservoir 102 is filled with an extinguishing fluid and is equipped with a discharge head that has a disc that closes the reservoir 102 and an explosive cartridge, and wherein the neck is fluidically connected to the discharge pipe 104 via the discharge head. When necessary, an activation order is sent to the explosive cartridge so that this explodes so as to destroy the disc and thus release the extinguishing fluid that flows in the discharge pipe 104. In the embodiment of the disclosure herein that is presented here, there is a single assembly 150, but depending on the quantity of extinguishing fluid required, it is possible to put in place a plurality of assemblies 150.

The structure 152 is fastened inside the pylon 12 by any appropriate securing mechanism such as bolts, for example. The pylon 12 has a wall with a window 60 passing through it that alternately allows the reservoir 102 to be introduced or withdrawn, in particular when it needs to be replaced. The reservoir 102 is introduced or withdrawn in a direction of introduction T that passes through the window 60 and in this case is parallel to the transverse direction Y.

Figure 6:
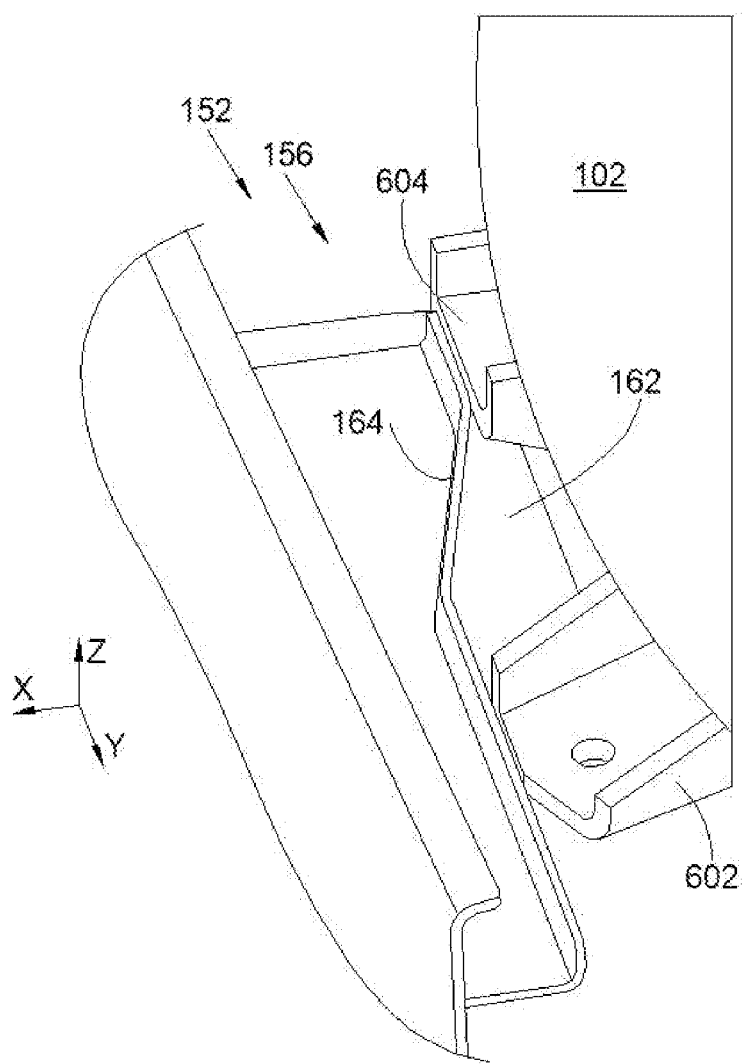
FIG. 6 is a perspective view of a part of the assembly according to the disclosure herein in a premounting position.
Figure 7:
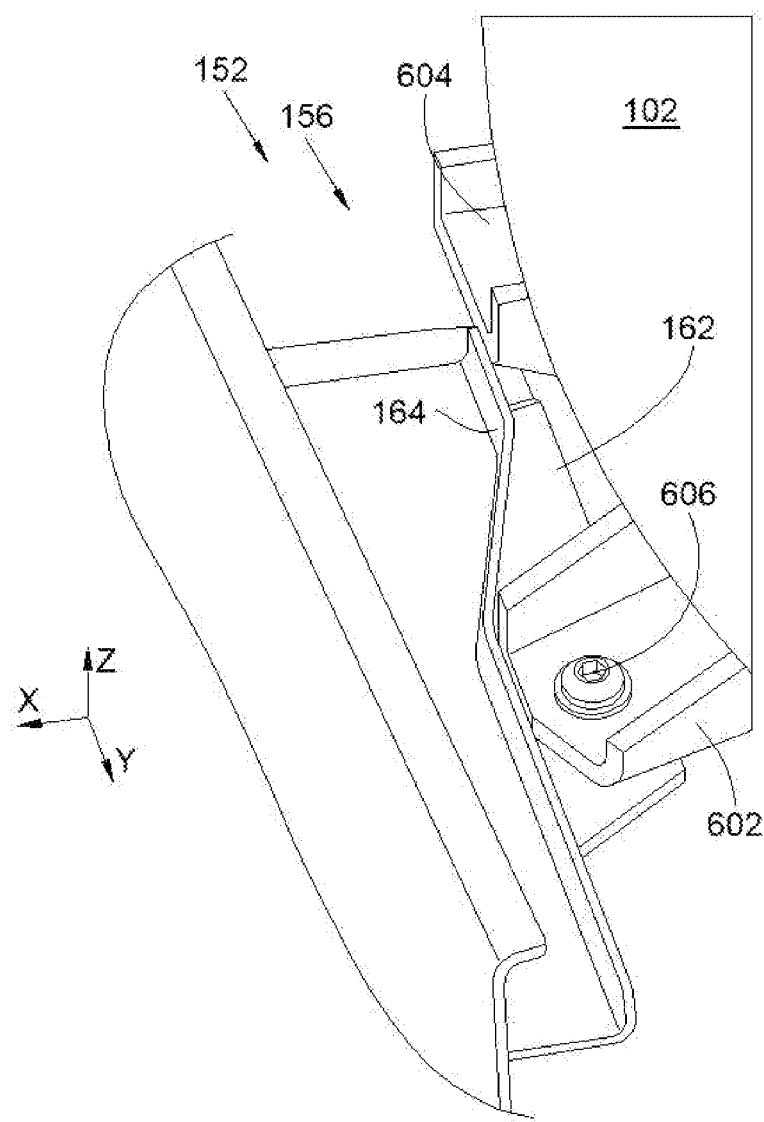
FIG. 7 is a perspective view of a part of the assembly according to the disclosure herein in a mounting position.

FIGS. 6 and 7 show design details of the disclosure herein and in particular of the reservoir 102.

In this case, the reservoir 102 takes the form of a sphere and it has two fastening tabs 602 and two bearing tabs 604 distinct from the fastening tabs 602. The reservoir 102 also has a peg 160 of which the axis is parallel to the direction of introduction T.

There is one fastening tab 602 and one bearing tab 604 on each side of the reservoir 102, and in this case they are disposed symmetrically with respect to a vertical plane of symmetry of the reservoir 102.

Figure 3:
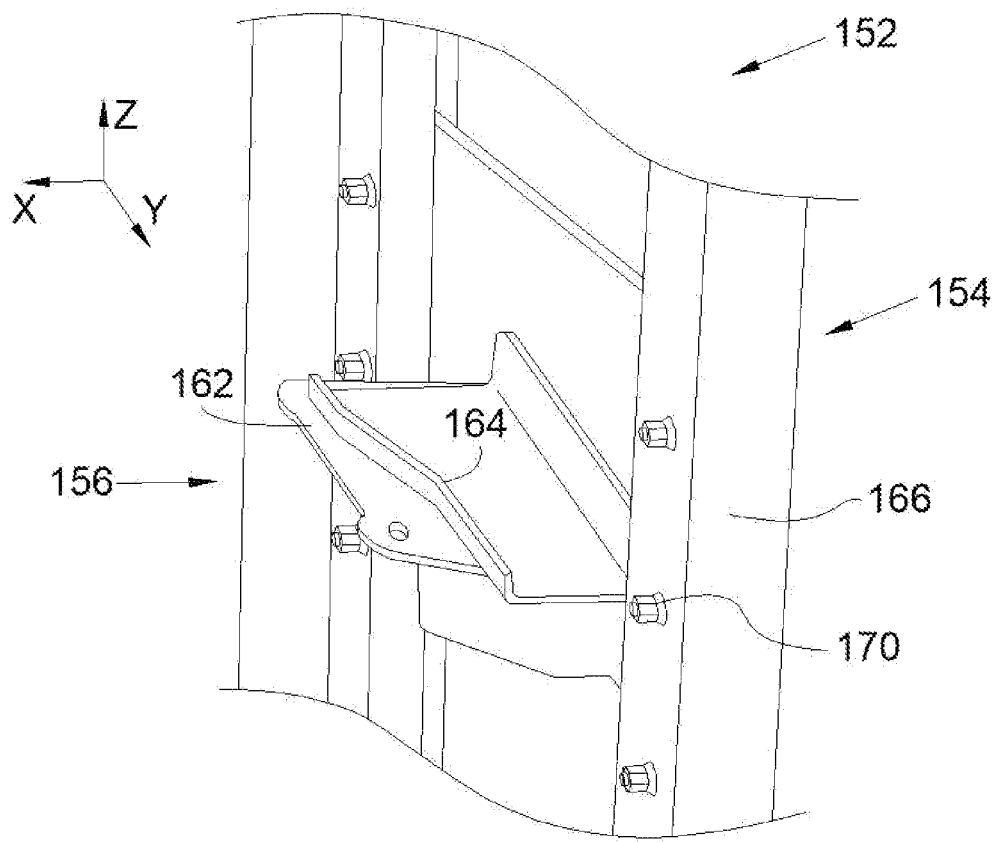
FIG. 3 is a perspective view of a part of a structure of the assembly according to the disclosure herein with the reservoir removed.
Figure 4:
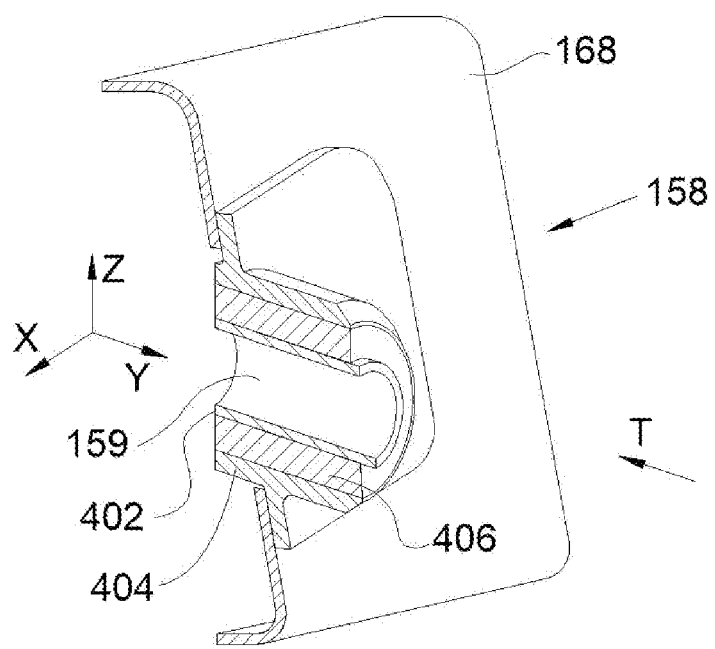
FIG. 4 is a perspective cross-sectional view of the structure in FIG. 2 on the plane IV.

FIGS. 3 and 4 show design details of the disclosure herein and in particular of the structure 152.

The structure 152 has a chassis 154 fastened inside the pylon 12 to a structure of the pylon 12, two supports 156 fastened to the chassis 154 and a nesting system 158 also fastened to the chassis 154 that has a bore 159 of which the axis is parallel to the direction of introduction T and of which an opening is oriented towards the window 60.

Each support 156 has a plate 162 fastened to the chassis 154 and a guide 164 fastened to the plate 162. The two supports 156 are disposed on either side of the reservoir 102, in this case on either side of the vertical plane of symmetry of the reservoir 102.

When the reservoir 102 is put in place, it passes through the window 60 and passes successively from a premounting position to a mounting position. The reservoir 102 is thus able to move in translation parallel to the direction of introduction T between the premounting position and the mounting position when it is put in place and vice versa when it is withdrawn.

FIG. 6 shows the premounting position in which each fastening tab 602 and each bearing tab 604 rest on one of the plates 162 and each guide 164 guides the fastening tab 602 and the bearing tab 604 that are associated with the plate 162 transversely with respect to the direction of introduction T, i.e. in this case parallel to the longitudinal direction X. Bearing on four tabs during the premounting makes it possible to ensure a stable position of the reservoir 102 and such guiding makes it possible to align the peg 160 and the opening of the bore 159 of the nesting system 158, even without visibility for the technician performing the placement.

FIG. 7 shows the mounting position in which each fastening tab 602 rests on the associated plate 162 and the peg 160 is introduced into the opening of the bore 159 of the nesting system 158. Each fastening tab 602 is fastened to the associated plate 162 by any appropriate securing mechanism such as bolts 606, for example. In this mounting position, the bearing tabs 604 no longer rest on the plates 162. The reservoir 102 is then fastened to the structure 152 by the two fastening tabs 602 and the peg 160. Such an arrangement makes it easier to put the reservoir 102 in place even when is has large dimensions.

In the embodiment of the disclosure herein that is presented in FIG. 2, the chassis 154 has two parallel frames 166 disposed in this case on either side of the plane of symmetry of the reservoir 102 and a crossmember 168 that connects the two frames 166 to each other.

Each plate 162 is fastened to one of the frames 166 and two plates, and the crossmember 168 bears the nesting system 158, i.e. the crossmember 168 is on the opposite side with respect to the window 60.

Figure 5:
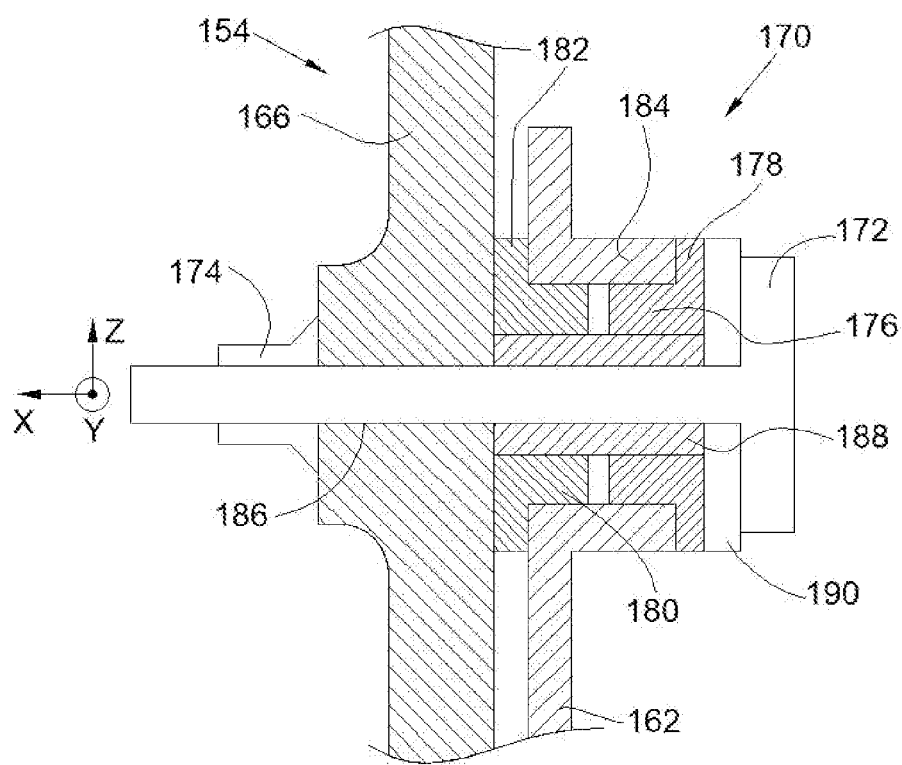
FIG. 5 is a cross-sectional view of a damping system implemented in the assembly according to the disclosure herein.

In order to limit the transfer of the surrounding vibrations to the reservoir 102, each plate 162 is fastened to the chassis 154 by at least one damping system 170 of which there are in this case six per plate 162 and of which an example is shown in greater detail in cross section in FIG. 5.

The damping system 170 has:
a screw 172 with a head and a threaded shank of which the axis is in this case transverse with respect to the direction of introduction T,
a nut 174,
a first ring 176 made of elastomer that has a first shoulder 178,
a second ring 180 made of elastomer that has a second shoulder 182,
an outer bearing 184 as one with the plate 162.

The first ring 176 is threaded onto the threaded shank with the first shoulder 178 against the head of the screw 172, the outer bearing 184 is threaded onto the threaded shank and is fitted onto the first ring 176, the second ring 180 is threaded onto the threaded shank, being fitted beneath the outer bearing 184 and with the second shoulder 182 away from the first shoulder 178 so as to bear against the chassis 154, in this case the frame 166, the threaded shank is introduced into a bore 186 of the chassis 154, in this case of the frame 166, and the nut 174 is tightened on the threaded shank on the other side of the chassis 154 with respect to the head.

After mounting, the damping system 170 successively comprises the head of the screw 172, the first shoulder 178, the outer bearing 184 fitted onto the first ring 176 and the second ring 180, the second shoulder 182, the chassis 154 and the nut 174.

The outer bearing 184 is thus sandwiched between the first shoulder 178 and the second shoulder 182.

By the presence of the two rings 176 and 180 that surround the outer bearing 184, preventing direct contact with the chassis 154, the vibrations transmitted to the plate 162 and therefore to the reservoir 102 are very effectively attenuated.

Furthermore, the use of a guide and fastenings made of elastomer material makes it possible, by virtue of the relative elasticity conferred on the interfaces, to absorb the manufacturing and assembly tolerances and thus to ensure that it is possible to mount the assembly on the structure of a pylon under any circumstances.

In the embodiment of the disclosure herein that is presented here, the damping system 170 also has an inner bearing 188 that is threaded onto the threaded shank and on which the two rings 176 and 180 are fitted, and a washer 190 that comes beneath the head so as to enlarge the area of contact with the first shoulder 178. Contact between the first shoulder 178 and the head is then made via the washer 190. The inner bearing 188 makes it possible to limit the compression of the shoulders of the elastomer rings to a predefined value, which is realized during the nominal torque tightening of the bolt. Since elastomers are known to flow under continuous load, this ring thus ensures that the tightening is carried out on a stack of rigid components and therefore the absence of subsequent loosening of the assembly.

In order to limit the transfer of the vibrations, the nesting system 158 also has damping. The nesting system 158 has:
an inner tube 402 of which the bore forms the bore 159 for housing the peg 160, i.e. the axis of the inner tube 402 is parallel to the direction of introduction T,
an outer tube 404 coaxial with the inner tube 402, disposed outside the inner tube 402, and fastened to the chassis 154, in this case to the crossmember 168, and
an intermediate tube 406 made of elastomer that is fastened between the inner tube 402 and the outer tube 404.

While at least one example embodiment of the invention (s) is disclosed herein, it should be understood that modifications, substitutions and alternatives may be apparent to one of ordinary skill in the art and can be made without departing from the scope of this disclosure. This disclosure is intended to cover any adaptations or variations of the example embodiment(s). In addition, in this disclosure, the terms "comprise" or "comprising" do not exclude other elements or steps, the terms "a", "an" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. An assembly comprising:
a structure having:
a chassis;
two supports; and
a nesting system fastened to the chassis and having a bore with an opening;
wherein an axis of the opening is parallel to a direction of introduction; and
wherein each of the two supports has a plate fastened to the chassis and a guide that is a unitary structure with the plate;
a reservoir containing an extinguishing fluid, wherein the reservoir comprises:
two fastening tabs;
two bearing tabs distinct from the fastening tabs; and
a peg, wherein an axis of the peg is parallel to the direction of introduction; and
a fastener;
wherein the reservoir is movable in translation parallel to the direction of introduction between:
a premounting position, in which each fastening tab and each bearing tab are positioned to rest on one of the plates and each guide is positioned to guide the fastening tab and the bearing tab, both of which are associated with the plate, transversely with respect to the direction of introduction to align the peg and the opening of the bore of the nesting system; and
a mounting position, in which each fastening tab is positioned to rest on one of the plates associated with such fastening tab, the peg is in the opening of the bore of the nesting system, the bearing tabs do not rest on the one of the plates, and the fastener is positioned to fasten each of the two fastening tabs to the one of the plates associated with such fastening tab.

2. The assembly according to claim 1, wherein, for each of the two supports, the plate is fastened to the chassis by at least one damping system.

3. The assembly according to claim 2, wherein each damping system has:
a screw with a head and a threaded shank;
a nut;
a first ring that has a first shoulder, comprises an elastomer, and is threadably engaged with the threaded shank, such that the first shoulder is against the head;
a second ring that has a second shoulder and comprises an elastomer; and
an outer bearing that is a unitary structure with the plate of the one of the two supports which the damping system fastens to the chassis;
wherein the outer bearing is threadably engaged with the threaded shank and is fitted onto the first ring;
wherein the second ring is threadably engaged with the threaded shank, in a position beneath the outer bearing and with the second shoulder oriented away from the first shoulder and bearing against the chassis;
wherein the threaded shank is in a bore of the chassis; and
wherein the nut is threadably engaged on the threaded shank on an opposite side of the chassis with respect to the head.

4. The assembly according to claim 3, wherein:
the damping system has an inner bearing threadably engaged with the threaded shank; and
the two rings are on the inner bearing.

5. The assembly according to claim 3, wherein the damping system has a washer beneath the head of the screw.

6. The assembly according to claim 1, wherein the nesting system has:
- an inner tube comprising a bore that forms the bore for housing the peg;
- an outer tube that is coaxial with the inner tube, disposed outside the inner tube, and fastened to the chassis; and
- an intermediate tube that is fastened between the inner tube and the outer tube and comprises an elastomer.

7. An aircraft comprising:
- a pylon, wherein one wall of the pylon has a window; and
- the assembly according to claim 1;
- wherein the chassis is fastened inside the pylon; and
- wherein the opening of the bore is oriented towards the window.

* * * * *